United States Patent [19]

Seibert

[11] 4,405,641

[45] Sep. 20, 1983

[54] CONSISTENCY REGULATOR FOR COSMETIC AND PHARMACEUTICAL PREPARATIONS

[75] Inventor: Karl Seibert, Duren, Fed. Rep. of Germany

[73] Assignee: Akzona Incorporated, Asheville, N.C.

[21] Appl. No.: 280,037

[22] Filed: Jul. 6, 1981

[30] Foreign Application Priority Data

Jul., 1980 [DE] Fed. Rep. of Germany ....... 3026071

[51] Int. Cl.$^3$ ................... A01N 37/08; A61K 47/00
[52] U.S. Cl. .................................. 424/305; 424/365
[58] Field of Search ............................... 424/365, 305

[56] References Cited

U.S. PATENT DOCUMENTS

| | | |
|---|---|---|
| 3,073,706 | 1/1963 | Trebous et al. . |
| 3,127,440 | 3/1964 | Stans . |
| 3,914,131 | 10/1975 | Hutchison .............................. 424/64 |
| 4,066,789 | 1/1978 | Mores et al. ......................... 424/365 |
| 4,151,001 | 4/1979 | Anderson, Jr. . |

FOREIGN PATENT DOCUMENTS 2757278  5/1979  Fed. Rep. of Germany .
2011403  7/1979  United Kingdom .

Primary Examiner—Delbert R. Phillips
Assistant Examiner—F. T. Moezie
Attorney, Agent, or Firm—Francis W. Young; Robert F. Green

[57] ABSTRACT

The use of monocarboxylic-acid-2-hydroxyalkyl esters derived from long-chain epoxides containing at least about eight carbon atoms and aliphatic long-chain monocarboxylic acids containing at least about twelve carbon atoms, to regulate the consistency of cosmetic and pharmaceutical formulations, is disclosed.

The monocarboxylic-acid-2-hydroxyalkyl esters employed in the present invention may be utilized as substitutes for natural or synthetic wax-like consistency regulators, in particular for beeswax, in cosmetic and pharmaceutical formulations such as oil-in-water and water-in-oil emulsions, as well as anhydrous formulations.

7 Claims, No Drawings

CONSISTENCY REGULATOR FOR COSMETIC AND PHARMACEUTICAL PREPARATIONS

BACKGROUND OF THE INVENTION

The present invention relates to the use of certain consistency regulators in cosmetic and pharmaceutical formulations.

In general, cosmetic emulsions are composed of a fatty phase, which contains numerous raw materials, an aqueous phase, active materials and, if required, pigments, preservatives and coloring materials. In the fatty phase, in addition to emulsifiers, oil components and antioxidants, consistency regulators are employed to increase the viscosity and thus improve the consistency required for a stable emulsion system. Consistency regulators in water-in-oil emulsions, include, for example, beeswax, paraffin, petroleum jelly, microwax, as well as metal stearates. In oil-in-water emulsions it is customary to use spermaceti, fatty alcohols and glycerofatty acid esters.

One of the best known cosmetic waxes is beeswax which is utilized in creams, lipsticks and make-up. In addition, beeswax is employed in pharmaceutical formulations such as ointments. Due to the complex chemical composition of beeswax, the cosmetic chemist often encounters difficulties reproducing formulations. For this reason and the fact that there is an increasing shortage of beeswax, efforts to develop economically acceptable synthetic beeswax substitutes have intensified in recent years.

U.S. Pat. Nos. 3,745,033, 3,914,131 and 3,933,708, describe combinations of high-molecular, alkyl-substituted, branched monocarboxylic acids, microcrystalline petroleum waxes and glyceride mixtures as beeswax substitutes. It has been disclosed in the above-mentioned U.S. patents that esterification products of montanic acid, ethylene glycol and oxidized paraffin, as well as synthetic waxes obtained by the esterification of pentaerythritol with saturated fatty acids and maleic anhydride have been used as synthetic beeswax substitutes.

U.S. Pat. No. 3,073,706 refers to several esters of mono- and polycarboxylic acids with mono- and multivalent alcohols as synthetic wax components in floor care materials. U.S. Pat. No. 3,127,440 discloses the use of dialkyl esters ($C_{30}$-$C_{60}$) of 1,4-dicarboxylic acids in hard wax formulations. U.S. Pat. No. 4,151,001 describes a beeswax substitute consisting of a polyester reaction product as obtained by the reaction under esterification conditions of aliphatic alcohols and a glycol compound.

The use of mono- and dicarboxylic-2-hydroxyalkylesters as emulsifiers in water-in-oil emulsions has also been proposed. German published patent application disclosure No. 2,757,278, describes the use of these hydroxyalkylesters as water-in-oil emulsifiers in cosmetic emulsions. Dicarboxylic acids are indicated to be especially preferred carboxylic acid components. When monocarboxylic acids are used, it is recommended to use hydroxyl-, halogen- or ether-group-substituted, short-chain compounds.

Although many of the above-mentioned and other known synthetic beeswax substitutes now readily available are adequate to produce effective non-aqueous formulations, many impair the stability of a formulation in emulsion systems containing water. Although some economically feasible synthetic beeswax substitutes are available, there continues to be a need for economical consistency regulators suitable for use in cosmetic and pharmaceutical formulations.

An object of the present invention is to produce a class of synthetic consistency regulators for cosmetic and pharmaceutical emulsions, which does not exhibit the disadvantages of many of the currently available materials and exerts a positive influence of the consistency of emulsions and decorative cosmetics without reducing the storage stability.

SUMMARY OF THE INVENTION

In particular, the present invention relates to the use of monocarboxylic-2-hydroxyalkylesters of long-chain epoxides and aliphatic, long-chain monocarboxylic acids in cosmetic and pharmaceutical formulations as consistency regulators. The long-chain monocarboxylic acids employed as carboxylic acid components pursuant to the present invention are characterized as having a minimum chain length of 12 carbon atoms. The esters of the present invention may be utilized as substitutes for natural or synthetic wax-like consistency regulators, in particular beeswax, in cosmetic and pharmaceutical formulations such as oil-in-water and water-in-oil emulsions, as well as anhydrous formulations.

Thus, in one embodiment, the present invention provides a cosmetic or pharmaceutical preparation containing an effective amount of a consistency regulator comprising a monocarboxylic-2-hydroxy-alkylester or mixture thereof, made by reacting under esterification conditions one or more monocarboxylic acids containing at least twelve carbon atoms with one or more 1,2-alkylene oxides containing from about 8 to about 40 carbon atoms.

In a further embodiment, the present invention provides a cosmetic or pharmaceutical emulsion comprising a fatty phase, an aqueous phase, and an effective amount of a consistency regulator comprising a monocarboxylic-2-hydroxy-alkylester, or mixture thereof made by reacting under esterification conditions one or more monocarboxylic acids containing at least twelve carbon atoms with one or more 1,2-alkylene oxides containing from about 8 to about 40 carbon atoms.

DETAILED DESCRIPTION OF THE PREFERRED EMBODIMENTS

As indicated, the present invention relates to cosmetic or pharmaceutical preparations containing an effective amount of a consistency regulator in accordance with the teachings herein. For purposes of this invention, a cosmetic or pharmaceutical preparation includes any topically applied preparation, such as skin-contacting preparations. Typically, some active ingredient would also be present in such preparations, such as a pharmaceutically active material or a cosmetically useful material. Such preparations primarily are in the form of water-in-oil or oil-in-water emulsions, but the present invention is not limited to the use of the described consistency regulator in emulsions and thus preparations containing solely an oily phase would be within the scope of the present invention.

Typically, the consistency regulators of the present invention will be employed in amounts from about 0.5 to about 20 percent, based on the total weight of the preparation.

The monocarboxylic-2-hydroxyalkylesters of the present invention may be prepared in accordance with known techniques by reacting monocarboxylic acids with epoxides under customary conditions. Suitable carboxylic acids include: stearic acid, isostearic acid, 12-hydroxystearic acid, wax acids, Koch's acids and telomeric acids. The useful carboxylic acids, as stated, contain at least 12 carbon atoms and may contain up to about 40 carbon atoms. Typically the acids will contain from about 12 to about 30 carbon atoms. Preferably 12-hydroxystearic acid is employed.

Epoxides suitable for reaction with the monocarboxylic acids are monomeric aliphatic unsubstituted 1,2-alkylene oxides, which may be obtained in accordance with known techniques from the corresponding olefins, or olefin mixtures, such as: 1,2-epoxyoctane, 1,2-epoxynonane, 1,2-epoxydecane, 1,2-epoxyundecane, 1,2-epoxydodecane, 1,2-epoxytridecane, 1,2-epoxytetradecane, 1,2-epoxypentadecane, 1,2-epoxyhexadecane, 1,2-epoxyheptadecane, 1,2-epoxyoctadecane, 1,2-epoxynonadecane, 1,2-epoxyeicosane, 1,2-epoxyuneicosane, 1,2-epoxydocosane, 1,2-epoxytricosane, 1,2-epoxytetracosane, 1,2-epoxypentacosane, 1,2-epoxypentacosane, 1,2-epoxyhexacosane, 1,2-epoxyheptacosane, 1,2-epoxyoctacosane, 1,2-epoxynonacosane, 1,2-epoxytriacontane, 1,2-epoxyuntriacontane, 1,2-epoxydotriacontane, 1,2-epoxytritriacontane, 1,2-epoxytetratriacontane, 1,2-epoxypentatriacontane, 1,2-epoxyhexatriacontane, 1,2-epoxyheptatriacontane, 1,2-epoxyoctatriacontane, 1,2-epoxynonatriacontane and 1,2-epoxytetracontane. In general, mixtures of epoxides are employed. The epoxides may contain from about 8 to about 40 carbon atoms and usually it is preferred to employ 1,2-alkylene oxides with about 16 to about 30 carbon atoms in the molecule.

The preparation of the present invention may optionally contain from 1 to about 20 percent of free carboxylic acids, based on the weight of the hydroxyalkylester constituent. The free carboxylic acids are preferably the same acids as were utilized to make the hydroxyalkylesters.

The monocarboxylic-2-hydroxyalkylesters of the present invention are suitable as consistency regulators in cosmsetic and pharmaceutical preparations. Their characteristics with respect to application technology, such as improvement in consistency and oil-binding capacity, are equal, and in certain instances superior, to natural beeswax, and exert a positive influence on the stability of emulsions. As a consequence, the hydroxyalkylesters of the present invention may be used as a substitute for natural beeswax in cosmetic and pharmaceutical preparations, such as oil-in-water and water-in-oil emulsions, as well as in non-aqueous preparations such as ointments or sticks.

The hydroxyalkylesters of the present invention may totally or in part replace natural and synthetic waxes or wax-like consistency regulators, that are commonly used in such formulations. The high compatability of the hydroxyalkylesters of the present invention with customary oil components, waxes and other additives in cosmetic and pharmaceutical preparations is also an advantage. In addition, a special advantage of the hydroxyalkylesters of the present invention when compared with natural waxes, is that they may be prepared with a quality that is always constant, so that fluctuations in the consistency and stability characteristics of the end products are avoided.

The esters of the present invention possess good stability with respect to hydrolytic splitting and are chemically resistant to oxidative influences. When hydroxyalkylesters having free carboxylic acids are used, a stable emulsion is obtained without the addition of borax. As a result, the emulsion will meet the demands made upon high-quality preparations as regards consistency and skin sensations.

For the purpose of giving those skilled in the art a better understanding of the present invention, the following illustrative, non-limiting examples are given. Unless otherwise indicated, all data concerning constituents or percentages are by weight.

EXAMPLE 1

Preparation of a Stearic-2-hydroxy-$C_{24/28}$-alkylester.

In a one liter three-necked flask equiped with a stirrer, descending cooler, thermometer and gas inlet tube, 364.65 g of $C_{24/28}$ epoxide (0.843 mol) are melted under atmospheric pressure at a temperature from 70° to 80° C. To the melted epoxide is added a mixture of 235.35 g of stearic acid (0.843 mol) and 0.78 g of triethylamine (0.13% by weight). The resulting melt is heated to 180° C. within 30 minutes and stirred for 5 hours at this temperature, while continuously passing nitrogen gas through the reaction mixture. About 3 g of water are split off. To the reaction mixture is added 105.88 g of hydroxystearic acid. The resulting mixture is stirred for 1.5 hours at 180° C. The reaction mixture is cooled to 80° C. and decanted. The product has the following characteristics: Appearance—beige—colored wax; color (Gardner) 6–7; acid number=26; saponification number=103; fusion point=55°–57° C.

Employing the monocarboxylic-2-hydroxyalkylester prepared in Example 1, the following water-in-oil creams and stick formulations are prepared:

EXAMPLE 2

Water-in-Oil Cream

Stearic-2-hydroxy-$C_{24/28}$-alkylester: 5.0 parts by weight
Copolymer of epoxydodecane and ethylene oxide: 3.0 parts by weight
Sorbitan monooleate: 3.0 parts by weight
Isopropyl stearate: 5.0 parts by weight
Paraffin oil: 15.0 parts by weight
p-Hydroxybenzoic ester: 0.2 parts by weight
Borax: 0.4 parts by weight
Sorbitol, 70%: 5.0 parts by weight
Water: 63.8 parts by weight
The fatty phase is melted at 75° C. until homogeneous. At the same time, the aqueous phase is also heated to 75° C. and is then slowly added to the fatty phase with initial rapid stirring. A soft cream is obtained, which does not lose its consistency even at 45° C.

EXAMPLE 3

Cleansing Cream

Stearic-2-hydroxy-$C_{24/28}$-alkylester: 14.0 parts by weight
Isopropyl myristate: 5.0 parts by weight
Copolymer of epoxydodecane and ethylene oxide: 4.0 parts by weight
Paraffin oil: 36.0 parts by weight
p-Hydroxybenzoic ester: 0.2 parts by weight
Borax: 1.0 parts by weight
Water: 39.8 parts by weight
The fatty phase is heated to 75° C. The aqueous phase is prepared simultaneously and also is heated to 75° C. The fatty phase is emulsified with the aqueous phase, with rapid stirring, and subsequently cooled. A perfume oil is added at 45° C. to produce a very greasy cleansing cream, which is suitable for the removal of make-up and other decorative cosmetic products.

EXAMPLE 4

Lipstick of High Gloss

Stearic-2-hydroxy-$C_{24/28}$-alkylester: 10.0 parts by weight
Candelilla wax: 5.0 parts by weight
Carnauba wax: 2.0 parts by weight
Micro wax: 5.0 parts by weight
Castor oil: 59.85 parts by weight
Copolymer of epoxydodecane and ethylene oxide: 3.0 parts by weight
Isopropyl lanolate: 5.0 parts by weight
Preservative: 0.15 parts by weight
Color pigment: 5.0 parts by weight
Pearly luster pigment: 5.0 parts by weight The basic mass is heated until it is a homogeneous melt and the pigments are stirred into the melt. The finished mass is then homogenized via a three-roll mill, melted again, and a pearly luster pigment added. The resulting mass is then cast into molds. A solid mass is obtained which can easily be applied to the lips. A lipstick prepared in this manner has high surface brilliance. It has good storage stability and within a 3 month period, there was no oil separation at temperatures of 45° C. and −5° C.

For purposes of comparison, the monocarboxylic-2-hydroxyalkylesters pursuant to the invention (from long-chain epoxides and long-chain monocarboxylic acids), and mono- and dicarboxylic-2-hydroxyalkylesters of short-chain mono- and dicarboxylic acids (pursuant to German published patent application No. 2,757,278) were employed as consistency regulators. They were used in the formulation according to Example 2, in place of the stearic-2-hydroxy-$C_{24/28}$-alkylester pursuant to the invention. The use of adipic-di-2-hydroxy-$C_{12/14}$-alkylester, lactic-2-hydroxy-$C_{16/18}$-alkylester and of chloroacetic-2-hydroxy-$C_{24/28}$-alkylester produces unstable emulsions. In addition, the storage stability of such emulsions is completely inadequate. Phase separation already occurs after a short time.

Although the present invention has been described in conjunction with preferred embodiments, it is also understood that modification and variations may be resorted to without departing from the spirit and scope of the invention as those skilled in the art readily understand. Such modifications and variations are considered to be within the scope of the present invention and claims.

What is claimed is:

1. A cosmetic or pharmaceutical preparation comprising an effective amount of a pharmaceutically active material or a cosmetically useful material and an effective amount of a consistency regulator comprising a monocarboxylic-2-hydroxy-alkylester or mixture thereof made by reacting under esterification conditions one or more monocarboxylic acids containing at least twelve carbons atoms with one or more 1,2-alkylene oxides containing from about 8 to about 40 carbon atoms.

2. A cosmetic or pharmaceutical preparation comprising an effective amount of a pharmaceutically active material or a cosmetically useful material, a fatty phase, an aqueous phase, and an effective amount of a consistency regulator comprising a monocarboxylic-2-hydroxy-alkylester or mixture thereof made by reacting under esterification conditions one or more monocarboxylic acids containing at least twelve carbon atoms with one or more 1,2-alkylene oxides containing from about 8 to about 40 carbon atoms.

3. The preparation of claim 1 or 2 wherein the acids are selected from the group consisting of stearic acid, isostearic acid, 12-hydroxystearic acid, wax acids, and the 1,2-alkylene oxides are selected from the group consisting of 1,2-epoxyoctane, 1,2-epoxynonane, 1,2-epoxydecane, 1,2-epoxyundecane, 1,2-epoxydodecane, 1,2-epoxytridecane, 1,2-epoxytetradecane, 1,2-epoxypentadecane, 1,2-epoxyhexadecane, 1,2-epoxyheptadecane, 1,2-epoxyoctadecane, 1,2-epoxynonadecane, 1,2-epoxyeicosane, 1,2-epoxyuneicosane, 1,2-epoxydocosane, 1,2-epoxytricosane, 1,2-epoxytetracosane, 1,2-epoxypentacosane, 1,2-epoxypentacosane, 1,2-epoxyhexacosane, 1,2-epoxyheptocosane, 1,2-epoxyoctacosane, 1,2-epoxynonacosane, 1,2-epoxytriacontane, 1,2-epoxyuntriacontane, 1,2-epoxydotriacontane, 1,2-epoxytritriacontane, 1,2-epoxytetratriacontane, 1,2-epoxypentatriacontane, 1,2-epoxyhexatriacontane, 1,2-epoxyheptatriacontane, 1,2-epoxyoctatriacontane, 1,2-epoxynonatriacontane and 1,2-epoxytetracontane.

4. The preparation of claim 1 or 2 wherein the 1,2-alkylene oxides contain from about 16 to about 30 carbon atoms.

5. The preparation of claim 1 or 2 further comprising from about 1 to about 20 percent of free carboxylic acid, based on the weight of hydroxyalkylester present in the preparation.

6. The preparation of claim 1 or 2 wherein the consistency regulator is present in an amount from about 0.5 percent to about 20 percent, based on the total weight of the preparation.

7. The preparation of claim 6 wherein the hydroxyalkylester is stearic-2-hydroxy $C_{24/28}$-alkyl ester.

* * * * *

REEXAMINATION CERTIFICATE (595th)
United States Patent [19]
Seibert

[11] B1 4,405,641

[45] Certificate Issued Nov. 25, 1986

[54] CONSISTENCY REGULATOR FOR COSMETIC AND PHARMACEUTICAL PREPARATIONS

[75] Inventor: Karl Seibert, Duren, Fed. Rep. of Germany

[73] Assignee: Akzona Incorporated, Asheville, N.C.

Reexamination Request:
No. 90/000,899, Nov. 4, 1985

Reexamination Certificate for:
Patent No.: 4,405,641
Issued: Sep. 20, 1983
Appl. No.: 280,037
Filed: Jul. 6, 1981

[30] Foreign Application Priority Data

Jul. 10, 1980 [DE] Fed. Rep. of Germany ....... 3026071

[51] Int. Cl.$^4$ .................. A01N 37/08; A61K 47/00
[52] U.S. Cl. .................................... 514/785; 514/947

[58] Field of Search ............ 514/785, 947, 552; 424/70, 64

[56] References Cited

U.S. PATENT DOCUMENTS

| | | | |
|---|---|---|---|
| 3,906,106 | 9/1975 | Jacobi | 514/552 |
| 4,254,104 | 3/1981 | Suzuki | 424/70 |
| 4,292,088 | 9/1981 | Scheuffgen et al. | 424/64 |
| 4,303,639 | 12/1981 | Vanlerberghe | 424/63 |
| 4,389,346 | 6/1983 | Yamada et al. | 424/70 |

*Primary Examiner*—Delbert R. Phillips

[57] ABSTRACT

The use of monocarboxylic-acid-2-hydroxyalkyl esters derived from long-chain epoxides containing at least about eight carbon atoms and aliphatic long-chain monocarboxylic acids containing at least about twelve carbon atoms, to regulate the consistency of cosmetic and pharmaceutical formulations, is disclosed.

The monocarboxylic-acid-2-hydroxyalkyl esters employed in the present invention may be utilized as substitutes for natural or synthetic wax-like consistency regulators, in particular for beeswax, in cosmetic and pharmaceutical formulations such as oil-in-water and water-in-oil emulsions, as well as anhydrous formulations.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2 and 3 are determined to be patentable as amended.

Claims 4–7, dependent on an amended claim, are determined to be patentable.

1. A cosmetic or pharmaceutical preparation comprising an effective amount of a pharmaceutically active material or a cosmetically useful material and an effective amount of a consistency regulator comprising a [monocarboxylic-2-hydroxy-alkylester] *12-hydroxystearic-2-hydroxy-alkylester* or mixture thereof made by reacting under esterification conditions [one or more monocarboxylic acids containing at least twelve carbons atoms] *12-hydroxystearic acid* with one or more 1,2-alkylene oxides containing from about 8 to about 40 carbon atoms.

2. A cosmetic or pharmaceutical preparation comprising an effective amount of a pharmaceutically active material or a cosmetically useful material, a fatty phase, an aqueous phase, and an effective amount of a consistency regulator comprising a [monocarboxylic-2-hydroxy-alkylester] *12-hydroxystearic-2-hydroxy-alkylester* or mixture thereof made by reacting under esterification conditions [one or more monocarboxylic acids containing at least twelve carbon atoms] *12-hydroxystearic acid* with one or more 1,2-alkylene oxides containing from about 8 to about 40 carbon atoms.

3. The preparation of claim 1 or 2 wherein the [acids are selected from the group consisting of stearic acid, isostearic acid, 12-hydroxystearic acid, wax acids, and the] 1,2-alkylene oxides are selected from the group consisting of 1,2-epoxyoctane, 1,2-epoxynonane, 1,2-epoxydecane, 1,2-epoxyundecane, 1,2-epoxydodecane, 1,2-epoxytridecane, 1,2-epoxytetradecane, 1,2-epoxypentadecane, 1,2-epoxyhexadecane, 1,2-epoxyheptadecane, 1,2-epoxyoctadecane, 1,2-epoxynonadecane, 1,2-epoxyeicosane, 1,2-epoxyuneicosane, 1,2-epoxydocosane, 1,2-epoxytriocosane, 1,2-epoxytetracosane, 1,2-epoxypentacosane, 1,2-epoxyhexacosane, 1,2-epoxyheptocosane, 1,2-epoxyoctacosane, 1,2-epoxynonacosane, 1,2-epoxytriacontane, 1,2-epoxyunitriacontane, 1,2-epoxydotriacontane, 1,2-epoxytritriacontane, 1,2-epoxytetretriacontane, 1,2-epoxypentatriacontane, 1,2-epoxyhexatriacontane, 1,2-epoxyheptatriacontane, 1,2-epoxyoctatriacontane, 1,2-epoxynonatriacontane and 1,2-epoxytetracontane.

* * * * *